United States Patent [19]

Galleguillos et al.

[11] Patent Number: 5,639,448
[45] Date of Patent: Jun. 17, 1997

[54] METHOD OF THERMO-STYLING HAIR

[75] Inventors: Ramiro Galleguillos, Glendale Heights; Darshna Bhatt, Schaumburg, both of Ill.

[73] Assignee: Helene Curtis, Inc., Chicago, Ill.

[21] Appl. No.: 241,287

[22] Filed: May 11, 1994

Related U.S. Application Data

[63] Continuation of Ser. No. 734,594, Jul. 23, 1991, abandoned.

[51] Int. Cl.$^6$ ................................................. A61K 7/11
[52] U.S. Cl. .............. 424/70.11; 424/45; 424/DIG. 1; 424/DIG. 2; 132/203; 132/211
[58] Field of Search ................... 424/70, 71, 45, 424/DIG. 1, DIG. 2, 70.11; 524/602; 132/211, 203

[56] References Cited

U.S. PATENT DOCUMENTS

| | | | |
|---|---|---|---|
| 3,734,874 | 5/1973 | Kibler et al. | 524/602 |
| 3,850,178 | 11/1974 | Schoenholz | 132/211 |
| 4,300,580 | 11/1981 | O'Neill et al. | 424/70.11 |
| 4,335,220 | 6/1982 | Coney | 523/455 |
| 4,897,262 | 1/1990 | Nandagiri et al. | 424/70.11 |
| 5,021,238 | 6/1991 | Martino et al. | 424/45 |
| 5,085,859 | 2/1992 | Halloran et al. | 424/DIG. 2 |
| 5,094,838 | 3/1992 | Benson et al. | 424/45 |
| 5,158,792 | 10/1992 | Pierce | 424/70.11 |
| 5,164,177 | 11/1992 | Bhatt et al. | 424/70.11 |

*Primary Examiner*—Raj Bawa
*Attorney, Agent, or Firm*—Marshall, O'Toole, Gerstein, Murray & Borun

[57] ABSTRACT

A method of thermally setting hair including the sequential steps of:

(a) applying a thermoplastic polyester fixative resin composition, having a pH less than about 5, to the hair prior to configuring the hair in a desired configuration;

(b) contacting the hair with a thermal appliance to heat the applied polyester to its glaze transition temperature;

(c) configuring the hair while the polyester is at a temperature of at least its glass transition temperature; and (d) cooling the polyester to a temperature below its glass transition temperature while the hair is in the desired configuration to harden the polyester in the shape of the configured hair. Preferably, the thermoplastic polyester fixative resin includes a plurality of neutralized sulfonate moieties, and has a glass transition temperature below about 120° C., and is solubilized or dispersed in water in an amount of about 0.1% to about 20%.

26 Claims, No Drawings

METHOD OF THERMO-STYLING HAIR

CROSS-REFERENCE TO RELATED APPLICATION

This is a continuation of U.S. patent application Ser. No. 07/734,594, filed Jul. 23, 1991, now abandoned.

FIELD OF THE INVENTION

The present invention is directed to an aqueous composition containing a thermoplastic aryl-sulfonated polyester that is applied onto hair, preferably prior to shaping the hair, to provide a hair styling aid useful in thermo-styling hair in a particular shape or configuration. More particularly, the present invention is directed to an aqueous hair thermo-styling aid containing amorphous polyesters having a glass transition temperature below about 120° C., preferably in the range of about 20° C. to about 80° C. and that, after application to the hair, can be repeatedly heated and softened up to at least about 200° C. without thermal degradation to form the hair in a desired configuration, and the heating removed while the hair is in the desired configuration to allow the polymer to harden into a tough, clear film that retains the hair in the desired configuration. The polyesters can be shampooed out of the hair to avoid polymer build-up.

BACKGROUND OF INVENTION AND PRIOR ART

Normal hair can be so fine and limp, and so lacking in body that the hair does not hold a hair set well. Furthermore, the hair can become even less bodied and can be weakened further as a result of being subjected to chemically active hair treatments, such as permanent waves and tints. Additionally, hair can be weakened even further by other contributing factors, such as bleaching by sun exposure and/or chlorinated swimming pool water.

Normal hair is usually hydrophobic. However, many of the chemically active hair treatments remove the natural hydrophobic components from the hair. As a result, as the hydrophobicity of the hair decreases, the relative porosity of the hair increases and the hair tends to absorb water and swell more readily. In such a weakened and porous state, the water-swollen hair is more vulnerable to stretching and breaking.

Hair setting is basically the process of shaping wet hair by the steps of stretching the hair by curling the hair, fixing the hair in place by drying, then combing to give the finishing touches to provide the desired hairstyle. In particular, the setting of wet hair can be accomplished by making flat curls from strands of hair and fixing the curls with hairpins to produce "pin curls". Similarly, the wet hair can be set by using any of a variety of rollers or curlers to mechanically fix the hair. In either case, the winding of the wet hair is followed by drying, either by ambient air drying, electric drying or hot air drying.

The inherent problem encountered in hair setting is the natural tendency of the hair to return to its natural shape. For example, the set hair returns to its natural shape almost immediately if moistened. Likewise, high humidity conditions accelerate the tendency of the hair to return to its natural shape. Therefore, intensive efforts have been directed toward providing a hair set with sufficient holding power to maintain the designed hair style until at least the next shampoo, and, therefore, giving the hair set a degree of permanency.

As indicated by the natural tendency of hair to return to its natural shape, hair is an elastic structure. As a result, the slight deformations in the hair structure resulting from setting the hair are completely reversible. However, the rate of return of the hair to its natural shape is dependent upon the method used to deform, or set, the hair. Hair sets performed with wet strands of hair being rolled tightly, either in curls around the finger or on curlers, followed by drying the hair and unrolling the curlers after drying, corresponds to the release of the hair from a deformation-causing load. The deformation, or set, obtained can last for several days, but the set will not be retained if the hair is wetted.

The observations of hair deformation and relaxation are related to physical and chemical changes in the protein structure level of hair. Sufficient stretching of the hair causes partial transformation of the $\alpha$-keratin protein structure of the hair into the $\beta$-keratin protein structure of the hair. This structural transformation is accompanied by a shift in relative position of the polypeptide chains that is facilitated by water moistening the hair. The shift in position of the poypeptide chains therefore disrupts the ionic and hydrogen bonds in the hair. During the drying procedure, new ionic and hydrogen bonds are formed that block the return to the $\alpha$-keratin protein structure of hair. Gradually, the new protein linkages give way, under natural forces, such that the hair returns to its original state and length. If the hair is moistened, the return to the $\alpha$-keratin form is virtually immediate.

Therefore, investigators have sought to delay the combined action of natural forces and moisture that causes the hair to return to its original state by applying solutions containing naturally-occurring or synthetic polymers after the hair is shaped into a desired configuration. When applied to the shaped hair from aqueous or aqueous/alcoholic solutions (setting lotions), the polymers leave a film on the hair, after drying, to help maintain the hair in the previously shaped configuration. The polymeric film promotes cohesion and gives stability to the hair set to maintain the hold of the hair set. The principal objective of a setting lotion is to cover the previously styled hair with an invisible polymeric film that will give the styled hair a degree of rigidity and protect the hair style against wind and humidity.

Hair spray products act in a similar manner. The hair spray products are applied to wet and/or dry hair and contain a polymer, or mixtures of polymers, that remain fixed on the previously styled hair and affect the hair in various ways. For example, a "mechanical" effect is exerted on each individual hair. The film-forming polymers are used to provide a flexible sheath of polymeric film on the shaped hair after drying and, therefore, for mechanical reasons, retard the return of each individual hair to its natural shape. In addition, the polymeric film provides an overall stiffening of the hair. The hair behaves as if the individual hair strands are welded together, and the final hairstyle has better cohesion, therefore resisting the natural forces that return the hair to its natural shape. Finally, the polymeric film protects the hair from humidity. The ability of the polymeric film to attract and absorb water is preferably minimal, such that the polymeric film retards moisture uptake by hair and retards the return of the hair to the $\alpha$-keratin hair protein structure.

The general principles of hair setting are thoroughly discussed by C. Zviak, in *The Science of Hair Care*, Marcel Dekker, pp. 149–181 (1986). Zviak reviews both the polymers used in hair setting products and the formulation principles used to produce a hair set product that provides such beneficial hair set properties as improved hairstyle hold, easy application and combing, quick drying and non-stickiness, good hair body and bounce, increased hair volume and gloss, and hydrophobicity. It is evident that in the formulation of any end-use hair-styling product, some of these benefits must be sacrificed to some degree to achieve a competing benefit. Therefore, the formulation of hair set products has proved difficult, and, as a result, hair set products have been developed in a variety of product forms.

The prior art reveals that nonionic, cationic and anionic polymers have been used in hair set products, with the anionic polymers providing the best hair set results. However, anionic polymers also have disadvantages, such as high water solubility and, therefore, low hydrophobicity, and low substantivity to hair fibers, therefore, easy elimination from the hair by combing and brushing. As a result, investigators have continued to search for compounds and compositions that provide the primary benefit of improved durability of the hair set. As previously mentioned, to overcome some of the inherent disadvantages of the polymers utilized to set the hair, hair set products are made available in diversified forms in an attempt to minimize the drawbacks of the particular polymer used in the formulation. For example, hair set products are available as plasticizing lotions, plasticizing gels, aerosol foams, all-purpose lotions, hair sprays, holding lotions, conditioners and shampoos. In each case, however, the polymer is applied only to previously styled hair to help maintain the hair in the previously styled configuration.

In accordance with the present invention, a new and improved aqueous hair styling aid composition and method have been found wherein thermoplastic, amorphous polyester fixative resins or gums, having a glass transition temperature (Tg) less than about 120° C., is applied to wet or dry hair, preferably wet, before styling the hair in the final, desired configuration and, thereafter, the hair is heated to a temperature at or above the glass transition temperature of the polyester, while the hair is in the desired configuration, to soften the polyester, e.g., with a thermal appliance, such as a blow dryer or a curling iron. The polyester thereafter is cooled to a temperature below its glass transition temperature, e.g., by removal of the thermal appliance, to harden the polyester into a clear, tough polymeric film that provides durable set retention. This process of heating and cooling the applied polyester to set the hair can be repeated many times to reconfigure the hair without degrading the polyester. Further, the polyester can be removed by shampooing to prevent buildup of polymer on the hair.

SUMMARY OF THE INVENTION

In brief, the present invention is directed to an aqueous hair styling aid, in the form of a hair spray or mousse composition, and method of applying the composition to hair prior to substantial configuring of the hair in its final configuration; thereafter, heating the applied polymer to its glass transition temperature, while the hair is in the desired configuration, and thereafter removing the heat from the polymer to cool it to a temperature below its glass transition temperature to harden the polymer in the shape of the configured hair.

The aqueous composition of the present invention includes a water-dispersible thermoplastic polyester fixative resin in an amount of at least about 0.1% up to about 20% by weight of the composition, and preferably, in an amount in the range of about 0.5% to about 5% of the composition, particuarly about 0.5% to about 2% by weight of the composition. The compositions and method of the present invention are surprisingly more effective than application of the same resins in the manner of a hair spray coating over configured hair, in a lower polymer percentage, since the polymers are thermally softened and, thereafter, hardened when the hair is in the desired configuration. The amount of water in the compositions of the present invention can be in the range of about 30% to about 99.9% by weight of the composition; alcohol may be included in an amount of 0% to about 20% by weight; and, with aerosol compositions, a liquified propellant gas, such as dimethyl ether, is included in the compositions in an amount of about 5% to about 50% based on the total weight of the aerosol composition.

Accordingly, one aspect of the present invention is to provide a new and improved hair treating composition, and method, that can be applied to the hair from an aqueous composition prior to substantial configuring of the hair in a desired, final configuration in the form of an aerosol or non-aerosol hair spray, mousse, foam or gel for thermally retaining a particular shape or configuration of the hair.

Another aspect of the present invention is to provide an aqueous hair styling aid composition, and method, in the form of a hair spray, mousse, foam or gel, that can be heat softened with common hair treating thermal appliances, such as curling irons, hot crimpers, heated rollers, hair dryers or other types of hair heating devices used for drying or shaping of hair; wherein the composition includes a thermoplastic polymer capable of hardening rapidly, while the hair is in a desired configuration, upon removal of the thermal appliance from the hair, to provide a durable hair set.

Another aspect of the present invention is to provide a hair styling aid composition, and method of configuring or styling hair, in the form of a hair spray, mousse, foam or gel that includes water in an amount of about 30% to about 99.9% by weight of the composition; and a thermoplastic polyester fixative polymer that includes a plurality of sulfonated dicarboxylic acid moieties and/or neutralized sulfonate moieties, and has a glass transition temperature below about 120° C., that is solubilized or dispersed in the water in an amount of about 0.1% to about 20%, preferably about 0.5% to about 2% by weight of the composition.

Still another aspect of the present invention is to provide a new and improved aerosol or non-aerosol hair styling aid composition, that includes water in an amount of about 30% to about 99.9% by weight of the composition; a thermoplastic polyester fixative polymer containing a plurality of sulfonated aromatic dicarboxylic acid moieties and having a glass transition temperature less than about 120° C., and preferably less than about 100° C., that is solubilized in the water in an amount of about 0.1% to about 10% by weight of the composition; alcohol in an amount of 0% to about 30%, preferably about 5% to about 25% by weight; and a propellant gas for aerosol compositions.

Still another aspect of the present invention is to provide a new and improved aerosol or non-aerosol hair styling aid composition, that includes water in an amount of about 30% to about 99.9% by weight of the composition; a thermoplastic polyester fixative polymer containing a plurality of sulfonated aromatic dicarboxylic acid moieties and having a glass transition temperature less than about 120° C., and preferably less than about 100° C., that is solubilized in the water in an amount of about 0.1% to about 10% by weight of the composition; alcohol in an amount of 0% to about 30%, preferably about 5% to about 25% by weight; a conditioning agent in an amount of about 0.1% to about 10% by weight of the composition and a propellant gas for aerosol compositions.

DETAILED DESCRIPTION OF THE PREFERRED EMBODIMENT

The polymers or resins useful in the aqueous compositions of the present invention are homopolymers or copolymers that are, or can be rendered soluble by partial or complete neutralization of pendant sulfonic acid groups, in aqueous or hydroalcoholic carrier mixtures. To achieve the full advantage of the present invention, the fixative resin is an amorphous polyester that is dispersed or solubilized directly in water without the assistance of organic solvents, surfactants or amines. A simplified general structural formula for the polymers is as follows:

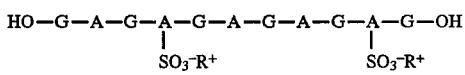

A=an aromatic dicarboxylic acid moiety

G=an aliphatic or cycloaliphatic glycol residue

OH=hydroxy end groups

R=H or a monovalent alkaline earth metal, e.g., Na, K, Li, and the like; a primary, secondary or tertiary amine, e.g., methyl amine, dimethyl amine, trimethyl amine; ammonium; or an alkanolamine, such as aminomethyl propanol, isopropanol amine, triisopropanol amine, ethanolamine, diethanolamine, triethanolamine, and the like.

While the structural formula for the polymer shows two $SO_3R$ substituents on dicarboxylic acid moieties of the polymer backbone, on average, there are five to eight $SO_3R$ substituents per polymer molecule. The weight average molecular weight of the polymers generally is less than about 200,000 to provide a Tg less than about 120° C. and, preferably, in the range of about 10,000 to about 50,000. The molecular weight, however, is not critical so long as the polymer has a Tg less than about 120° C.

Suitable polymers are sold by Eastman Corportion under the trademark EASTMAN AQ. EASTMAN AQ 29, for example, has a glass transition temperature of about 29° C. The dicarboxylic acid moieties have the general structural formula:

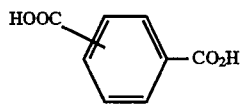

e.g., phthalic acid (ortho); isophthalic acid (meta); and terephthalic acid (para).

Accordingly, the sulfonic acid and metal sulfonates of these dicarboxylic acid moieties have the following general structural formulas and both sulfonic acid moieties and the neutralized sulfonic acid moieties can be included together in the polymer.

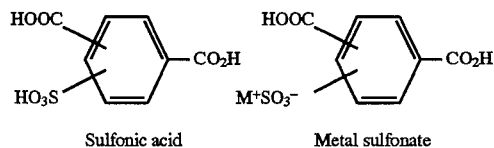

Sulfonic acid     Metal sulfonate

The aliphatic or cycloaliphatic glycol residues (G) have the following structural formulas:

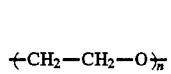     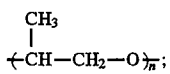

Polyethylene glycol     Polypropylene glycol

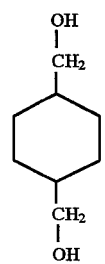     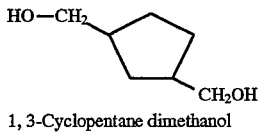

1,4-Cyclohexane dimethanol     1,3-Cyclopentane dimethanol where n=1 to about 200, preferably 1 to about 50.

Examples of the glycol residues are hexylene glycol; ethylene glycol; propylene glycol; 1,3 propane diol; 1,4 butane diol; 1,3 butane diol; 2,3 butane diol; 1,2-cyclopentane diol; 1,2-cyclohexane diol; pinacol; polyethylene glycol; polypropylene glycol, and the like.

Examples of these polymers include EASTMAN AQ Polymers 55, 38 and 29, which are water dispersible thermoplastic polymers including sodium sulfonate moieties. These are amorphous thermoplastic polyesters having good substantivity for hair. These polymers easily can be dispersed in warm and cold water, making them amenable for formulation and delivery from compressed aerosol and non-aerosol sprays, mousses, gels, lotions pomades, and the like, where the main carrier fluid is water, water/ethanol, water/isopropanol or water/water-soluble-glycol carrier mixtures. The amount of alcohol and/or glycol carrier that can be added to the solution depends on the type of resin. The tolerance decreases in the following order AQ 55<AQ 38<AQ 29. For instance, it has been found that aqueous solutions of AQ 55 can tolerate no more than about 8% by weight of ethanol, i.e., the polymer starts to precipitate. Where polymer precipitation occurs at a higher alcohol and/or glycol percentage, compatible suspending, and/or stabilizing agents can be included. AQ 38 and 29 can tolerate up to about 20% ethanol. Since the polymers disperse in water and do not dissolve, their viscosity never exceeds more than about 100 centipoises at a 20% polymer concentration. Therefore, the amount of polymer that can be used in this invention is from about 0.1% to about 20% by weight. The polyester solutions/dispersions are stable at pH's between 1 and 12, although pH's between 3 and 9 are desired in personal care products. A number of adjuvants such as surfactants, emollients, silicones, monovalent mineral salts, fragrance, and the like can be added as desired.

The polyesters have relatively low glass transition tempertures in the range of from about 20° C. to about 60° C. and soften and flow at temperatures below 100° C. Calorimetric experiments such as differential scanning calorimetry (DSC) and thermogravimetric analysis (TG) have shown that the resins do not chemically degrade upon repeated heating and cooling. These polymers, therefore, are exceptionally suitable for thermo-styling of hair with curling irons, hot crimpers, rollers, and any other hot device used in hair styling. It has been have found that the temperature of most hot hair styling devices ranges from about 80° C. to about 160° C.

Shaping of the hair is best accomplished by first applying the composition to hair while wet, allowing the hair to dry, and then physically shaping the hair with the hot styling aid. The heat softens the resin, thereby allowing it to spread along the hair shaft and acquire the configuration of the hot styling aid. After removing the hot styling aid, the resin hardens, maintaining the hair in the shape imparted by the styling aid. Because of the thermal stability of the resin, the hair can be restyled at any time, adding a convenience which is not possible to obtain with conventional hair fixative resins. Electron Scanning Microscopy (ESM) experiments on hair have shown that the main styling mechanism is not by gluing the hair fibers to one another, as is the case of conventional hair fixatives, but by coating the individual hair fibers with a hard, tough, thin film of resin which has enough mechanical strength to maintain the shape of the hair fiber. Coating of the hair fibers, and not gluing them together, also has the advantage of producing a durable hair style that easily can be combed through with less damage to hair.

Hair relaxation experiments have demonstrated that the shape of the hair (curls, waves, locks, zigzags, spirals, and the like) stays put until the hair is shampooed. Washability studies (optical and ESM) have shown that the resin can be washed out from the hair by simple shampooing. No resinous build-up was seen after five exaggerated cycles: treatment of hair with a 6% by weight solution, drying under air, hot curling for 30 seconds and washing with a solution of water and 10% sodium lauryl sulfate.

In accordance with another important feature of the present invention, any ionizable metal salt, wherein the metal has a valence of at least II, can be included in the composition, for polymer crosslinking, to improve the hair set retention properties of treated human hair. Hair treated with the aqueous thermoplastic polyester compositions of the present invention adjusted to a proper pH, e.g., above about 8.0, and containing an ionizable metal salt exhibits improved hair set retention properties if the metal of the ionizable metal salt has a valence of at least II.

For example, ionizable salts of the alkaline earth metals, such as magnesium, calcium and barium, have a valence of II, and, therefore, can be used alone or in combination in the composition of the present invention. Similarly, ionizable salts of aluminum, titanium, vanadium, manganese, mercury, cadmium, lead, iron, cobalt, nickel, silver, copper, cerium, hafnium, germanium, zinc and zirconium, or combinations thereof, are suitable for use in the present invention. In addition, any other ionizable metal salt, wherein the metal has a valence of at least II, can be used alone or in combination with the above-mentioned metals.

The anion of the ionizable metal salt can be any anionic moiety, either organic or inorganic in chemical structure, that permits or facilitates ionization of the ionizable metal salt in aqueous solution. The principal importance of the anion is to control release of the metal cation through ionization, and, therefore, the anion can be any of the halides, such as bromide or chloride, sulfate, nitrate, phosphate, acetate, lactate, or like organic and/or inorganic anions that easily dissociate and will not react with the hair or other composition components. Because the composition of the present invention is maintained at an acidic pH, anions such as hydroxyl, carbonate, and bicarbonate, are not suitable as the anion of the ionizable metal salt.

Particular ionizable metal salts of metals having a valence of at least two include, but are not limited, aluminum chloride, aluminum sulfate, aluminum lactate, calcium sulfate, cupric chloride, magnesium chloride, zinc chloride, and ferric chloride.

The polyesters can be crosslinked with polyvalent metal compounds such as those described in U.S. Pat. No. 3,850,178, hereby incorporated by reference. Other useful polyvalent metal compounds include those described in U.S. Pat. No. 4,036,241, at lower pH's, and this assignee's U.S. Pat. No. 4,960,588, both patents hereby incorporated by reference. An elegant, crosslinked polymer composition, preferred in accordance with the present invention is obtaining by first dispersing the resin in water, adding ammonium hydroxide to pH 9.0 or higher, then adding potassium or ammonium alum. The polyvalent metal preferably is present in an amount of at least 1.5% of metal by weight of the resin. The composition then is applied onto the hair while wet and the hair is allowed to dry. As the hair dries, some of the ammonium hydroxide will be lost as ammonia gas, leaving sulfonic acid groups free to react with the alum-derived Al $^{+3}$ atoms, as

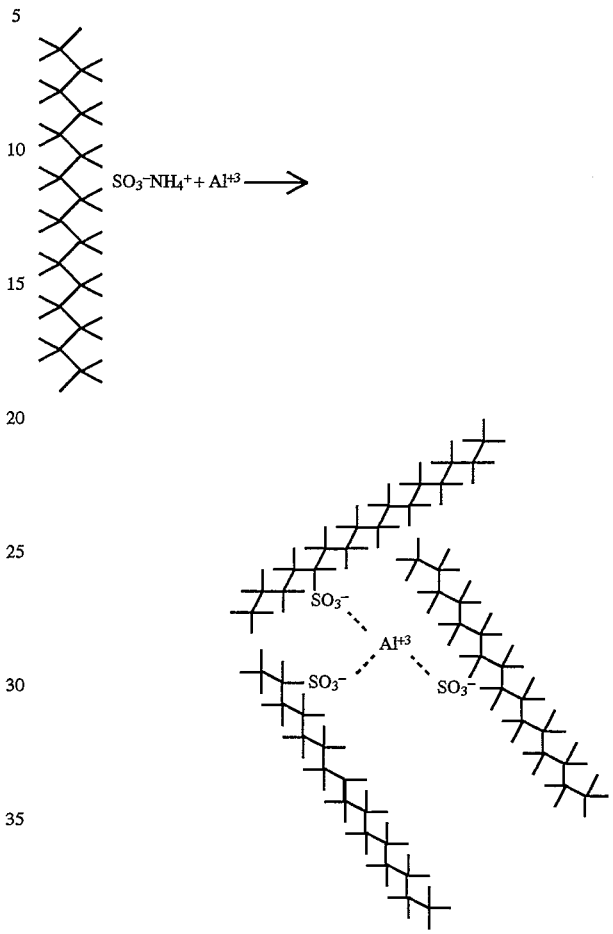

FORMULATION EXAMPLES

Example 1

| Hair Spray Concentrate: | | | |
|---|---|---|---|
| Item | Compound | | % Wt. |
| 1 | AQ 55 or 38 Polyester | = | 0.1 to 6% |
| 2 | Ethanol | = | 0 to 8% |
| 3 | Glycerine | = | 0 to 1% |
| 4 | Fragrance | = | as needed |
| 5 | Solubilizer | = | as needed |
| 6 | Water | = | Q.S. to 100% |

In formulating the composition of Example 1, item 1 is added first to water (item 6) until well dispersed. To this dispersion add items 2, 3, 4 and 5 in any order.

The above concentrate can be dispersed, as such, from a pump sprayer. It also can be used to make an aerosol product by charging the composition into an aerosol container with a suitable propellant gas, such as a hydrocarbon, a halogenated hydrocarbon, dimethyl ether (DME), carbon dioxide, compressed nitrogen, air, and the like. The preferred gas is DME in a composition (concentrate) to propellant ratio of about 65/35.

Example 2

| Item | Compound | | % Wt. |
|---|---|---|---|
| | Mousse: | | |
| 1 | AQ 55 or 38 | = | 0.1 to 6% |
| 2 | Anionic Surfactant | = | 0 to 0.5% |
| 3 | Nonionic Surfactant | = | 0 to 0.5% |
| 4 | Sandoperm FE | = | 0 to 2% |
| 5 | Fragrance | = | as needed |
| 6 | Propellant | = | 5 to 15% |
| 7 | Water | = | Q.S. to 100% |

In formulating the composition of Example 2, item 1 is first dispersed in water (item 7). The surfactants (items 2 and 3) are added and dispersed well. It is preferred to keep the level of surfactants as low as possible (preferably less than about 5% by weight and, more preferably, less than about 3% by weight) to avoid overplastization of the resin. Sandoperm FE or any other water-dispersible silicone, or other conditioning agent, can be added for conditioning benefits. Fragrance preferably is added last. This solution is placed in a mousse can or bottle and charged with propellant. Propellants can be any of the gases known in the art. It is preferred to use the hydrocarbon gases, e.g., isobutane or a blend of 89% by weight isobutane with 16% by weight propane, e.g., with DME: Hydrocarbon=3 to 7% by weight, and DME=7 to 3% by weight. The mousse foam of this formulation is excellent, rich, creamy and stable and easy to apply to hair.

In formulating aqueous or hydroalcoholic aerosol formulations, the long term stability of the aerosol composition is important because it affects its shelf life, product performance and delivery. Unstable solutions will usually exhibit some kind of phase separation such as two liquid phase formation or precipitation. Table I shows the results of stability tests at 110 deg F. of Eastman AQ 38 aerosol solutions using various buffers, polymers, salts, surfactants, oils, acids, chelating and suspending agents. Most stable aerosol solutions that use DME as the propellant are prepared when the pH of the solution is maintained below about 5, preferably below about 3.5. This can be accomplished, for example, by adding any mineral or water-soluble carboxylic acid.

TABLE I

Stability of 6% AQ 38 Aerosol Solutions
C/P = 70/30. Propellant = DME

| Ingredient | Concentration % wt. | obs. at 110° F. | pH |
|---|---|---|---|
| 6% AQ38/can | n/a | ppts/week | 6.805 |
| AMP | 1 drop | ppts/24 hrs | 10.05 |
| Lavender Oil | 0.1 | ppts/24 hrs | 6.70 |
| Oleth-2 | 0.1 | ppts/24 hrs | 6.75 |
| Lav/Oleth-2 | 0.1/0.1 | ppts/24 hrs | 6.74 |
| Prop. Glycol | 0.5 | ppts/24 hrs | 6.82 |
| Dibutylene Glycol | 0.5 | ppts/24 hrs | 6.73 |
| Finsolv TN | 0.5 | ppts/24 hrs | 6.82 |
| Citric Acid | 0.5 | Stable | 2.72 |
| Buffer 7 | 6 | ppts/24 hrs | 7.11 |
| Diethylene Glycol | 0.5 | ppts/24 hrs | 6.79 |
| Tetrasodium EDTA | 0.2 | ppts/36 hrs | 6.87 |
| Citric Acid | 0.01 | Stable | 4.47 |
| Na Acetate | 0.5 | ppts/36 hrs | 6.49 |
| Amphomer | 4 | ppts/36 hrs | 9.10 |
| Amphomer/NaCl | 3/0.5 | Stable/Hazy Mixture | 8.42 |
| NaCl/Citric Acid | 0.3/Q.A.to pH 4.9 | Stable/Hazy | 4.95 |
| Citric Acid | Q.A to pH 4.8 | Stable | 4.80 |

TABLE I-continued

Stability of 6% AQ 38 Aerosol Solutions
C/P = 70/30. Propellant = DME

| Ingredient | Concentration % wt. | obs. at 110° F. | pH |
|---|---|---|---|
| AQ38/NaCl | 0.25 | Stable/Hazy | 6.10 |
| AQ38/NaCl | 1 | White milky soln with ppts | 6.10 | ppts = precipitate
AMP = 2amino-2methyl-1propanol.
Finsolv TM = is trade name by Finetax for C 12–13 alcohols benzoate.
Buffer 7 is potassium phosphate monobasic sodium hydroxide buffer.
Amphomer is trade name by National Starch for octyl acrylamide/acrylates/butyl amino ethyl methacrylate coplymer.

With certain of the polymers, it may be advantageous to neutralize some sulfonic acid moieties to promote solubility/dispersibility. Neutralization and increased solubilization are accomplished with one or more inorganic bases, such as sodium hydroxide, potassium hydroxide, ammonium hydroxide and/or ammonium carbonate. Among stable organic bases are the water soluble bases, such as monoethanolamide (MEA), diethanolamine (DEA), triethanolamide (TEA), 2-methyl-2-amino-1-propanol (AMP), monoamino glycols, and the like, which help solubilize the polymer in water solutions. The level of neutralization required for solubilization varies for each polymer. All of the above-described polymers become soluble or readily dispersible in water and hydroalcoholic solutions at 100% neutralization, and all described levels of water/alcohol/propellant solutions. The pH of these solutions usually ranges from about 9 to about 12.

In accordance with one important embodiment, the composition of the present invention also includes from about 0.1% to about 10%, particularly about 0.5% to about 10%, and preferably from about 1.0% to about 5.0%, by weight of a non-volatile silicone compound or other conditioning agent(s), preferably a water-insoluble, emulsifiable conditioning agent. The preferred non-volatile silicone compound is a polydimethylsiloxane compound, such as a mixture, in about a 3:1 weight ratio, of a low molecular weight polydimethylsiloxane fluid and a higher molecular weight polydimethylsiloxane gum. The non-volatile polydimethylsiloxane compound is added to the composition of the present invention in an amount sufficient to provide improved combing and improved feel (softness) to the hair after shampooing. As referred to herein, "silicone gums" are those nonfunctional siloxanes having a viscosity of from about 5 to about 600,000 centistokes at 25° C. The so-called rigid silicones, as described in U.S. Pat. No. 4,902,499, herein incorporated by reference, having a viscosity above 600,000 centistokes at 20° C., e.g., 700,000 centistokes plus, and a weight average molecular weight of at least about 500,000 also are useful in accordance with the present invention.

Preferred silicone gums include linear and branched polydimethylsiloxanes, of the following general formula:

$(CH_3)_3SiO-[Si(CH_3)_2O]_n-Si(CH_3)_3$ , wherein n is from about 2,000 to about 15,000, preferably from about 2,000 to about 7,000. Silicone gums useful in compositions of the present invention are available from a variety of commercial sources, including General Electric Company and Dow Corning.

Another particularly suitable conditioning agent that can be included in the Composition of the present invention is a volatile hydrocarbon, such as a hydrocarbon including from about 10 to about 30 carbon atoms, that has sufficient volatility to slowly volatilize from the hair after application of the aerosol or non-aerosol styling aid composition. The volatile hydrocarbons provide essentially the same benefits as the silicone conditioning agents.

The preferred volatile hydrocarbon compound is an aliphatic hydrocarbon including from about 12 to about 24 carbon atoms, and having a boiling point in the range of from about 100° C. to about 300° C. Exemplary volatile hydrocarbons are depicted in general structural formula (I), wherein n ranges from 2 to 5,

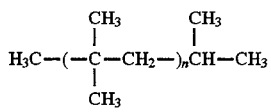

Examples of volatile hydrocarbons useful in the composition of the present invention are the commercially-available compounds PERMETHYL 99A and PERMETHYL 101A, corresponding to compounds of general structure (I) wherein n is 2 and 3, respectively, available from Permethyl Corporation, Frazer, Pa. A volatile hydrocarbon compound is useful in the composition of the present invention either alone, in combination with another volatile hydrocarbon, or in combination with a volatile silicone.

Examples of other suitable water-insoluble conditioning agents that can be incorporated into the aerosol or non-aerosol aqueous styling aid composition of the present invention include the following: polysiloxane polyether copolymers; polysiloxane polydimethyl dimethylammonium acetate copolymers; acetylated lanolin alcohols; dimethyl dialkyl ammonium chlorides; modified alkyl dimethyl benzyl ammonium chlorides; lauryl dimethylamine oxide; stearyl dimethyl benzyl ammonium chloride; a lanolin-derived extract of sterol on sterol esters; lanolin alcohol concentrate; an isopropyl ester of lanolin fatty acids; sulfur rich amino acid concentrates; isopropyl ester of lanolin fatty acids; stearyl dimethyl benzyl ammonium chloride; cetyl trimethyl ammonium chloride; oleyl dimethyl benzyl ammonium chloride; oleyl alcohol; stearyl alcohol; stearyl dimethyl benzyl ammonium chloride; stearamido-propyl dimethyl myristyl acetate; a polyol fatty acid; a fatty amido amine; guar hydroxypropyltrimonium chloride; cetyl/stearyl alcohol; quaternized protein; keratin protein derivatives; isostearamidopropyl dimethylamine; stearamidopropyl dimethylamine; cetrimonium bromide; myrtrimonium bromide; stearalkonium chloride; cetyl trimethyl ammonium chloride; laurylpyridinium chloride; tris(oligoxyethyl)alkyl ammonium phosphate; an amino-functional silicone; lapyrium chloride; isopropyl ester of lanolic acids; ethoxylated (30) castor oil; acetylated lanolin alcohol; fatty alcohol fraction of lanolin; a mineral oil and lanolin alcohol mixture; high molecular weight esters of lanolin; quaternium-75; vinylpyrrolidone/dimethylaminoethylmethacrylate copolymer; alkyl trimethyl ammonium chloride; 5 mole ethylene oxide adduct of soya sterol; 10 mole ethylene oxide adduct of soya sterol; stearic acid ester of ethoxylated (20 mole) methyl glucoside; sodium salt of poly-hydroxycarboxylic acid; hydroxylated lanolin; cocamidopropyl dimethylamine lactate; cocamidopropyl dimethylamine propionate; cocamidopropyl morpholine lactate; isostearamidopropyl dimethylamine lactate; isostearamidopropyl morpholine lactate; oleamidopropyl dimethylamine lactate; linoleamidopropyl dimethylamine lactate; stearamidopropyl dimethylamine lactate, ethylene glycol monostearate and propylene glycol mixture; stearamidopropyl dimethylamine lactate; acetamide MEA; lactamide MEA; stearamide MEA; behenalkonium chloride; behenyl trimethyl ammonium methosulfate and cetearyl alcohol mixture; cetearyl alcohol; isostearamidopropalkonium chloride; linoleamidopropalkonium chloride; oleyl dimethyl benzyl ammonium chloride; tallow imidazolinum methosulfate; stearyl dimethyl benzyl ammonium chloride; stearyl trimonium methosulfate; mixed ethoxylated and propoxylated long chain alcohols; stearamidopropyl dimethylamine lactate; polonitomine oxide; oleamine oxide; stearamine oxide; soya ethyldimonium ethosulfate; hydroxypropyl bislauryl-dimonium chloride; hydroxypropyl biscetyl-dimonium chloride; hydroxypropyl bisstearyl dimonium chloride; hydroxypropyl bisbehenyl dimonium chloride; ricinolamidopropyl ethyldimonium ethosulfate; olealkonium chloride; stearalkonium chloride; N-(3-isostearamidopropyl)-N,N-dimethyl amino glycolate; N-(3-isostearamidopropyl)-N,N dimethyl amino gluconate; hydrolyzed animal keratin; ethyl hydrolyzed animal keratin; stearyl ammonium chloride; stearamidoethyl diethylamine; cocamidopropyl dimethylamine; lauramidopropyl dimethylamine; oleamidopropyl dimethylamine; palmitamidopropyl dimethylamine; stearamidopropyl dimethylamine lactate; avocado oil; sweet almond oil, grape seed oil; jojoba oil; apricot kernel oil; sesame oil; hybrid safflower oil; wheat germ oil; cocamidoamine lactate; ricinoleamido amine lactate; stearamido amine lactate; stearamido morpholine lactate; isostearamido amine lactate; isostearamido morpholine lactate; wheat germamido dimethylamine lactate; behenamidopropyl betaine; ricinoleamidopropyl betaine; wheat germamidopropyl dimethylamine oxide; disodium isostearaimido MEA sulfosuccinate; disodium oleamide PEG-2 sulfosuccinate; disodium oleamide MEA sulfosuccinate; disodium ricinoleyl MEA sulfosuccinate; disodium wheat germamido MEA sulfosuccinate; disodium wheat germamido PEG-2 sulfosuccinate; stearalkonium chloride; stearly dimethyl benzyl ammonium chloride; stearamido amine; stearamido morpholine; isostearamido amine; isostearamido morpholine; polyethylene glycol (400) mono and distearates; synthetic calcium silicate; isostearic alkanolamide; ethyl esters of hydrolyzed animal protein; blend of cetyl and stearyl alcohols with ethoxylated cetyl or stearyl alcohols; amido amines; polyamido amines; palmityl amido betaine; propoxylated (1-20 moles) lanolin alcohols; isostearamide DEA; and hydrolyzed collagen protein.

When one or more of these water-insoluble conditioning agents is included in the composition of the present invention in an amount of about 0.5% to about 10% by total weight of the composition, the composition also can include a suspending agent for the conditioning agent, in an amount of about 0.5% to about 10%, by total weight of the composition. The particular suspending agent is not critical and can be selected from any materials known to suspend water-insoluble liquids in shampoo compositions. Suitable suspending agents are for example, distearyl amate (distearyl phthalamic acid); fatty acid alkanolamides; esters of polyols and sugars; polyethylene glycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCUTCHEON'S DETERGENTS AND EMULSIFIERS, 1989 Annual, published by McCutcheon Division, MC Publishing Co.

A nonionic alkanolamide also is optionally included in an amount of about 0.1% to about 5% by weight in the styling aid compositions that include a conditioning agent to provide exceptionally stable emulsification of water-insoluble conditioning agents and to aid in thickening and foam stability. Other useful suspending and thickening agents can be used instead of the alkanolamides such as sodium alginate; guar gum; xanthan gum; gum arabic; cellulose derivatives, such as methylcellulose, hydroxybutylcellulose, hydroxyethylcellulose, hydroxypropylcellulose and carboxymethylcellulose; and various synthetic polymeric thickeners, such as the polyacrylic acid derivatives. Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof. Other suitable suspending agents are disclosed in Oh et al. U.S. Pat. No. 4,704,272 Grote et al. U.S. Pat. No. 4,741,855; and Bolich, Jr. et al. U. S. Pat. No. 4,788,006, which patents are hereby incorporated by reference.

Emulsion stabilizers also may be used in compositions of the invention. Useful examples include, such compounds as polyethylene glycol, silicone copolyols, polyvinyl alcohol, sorbitan monostearate, oleth-2, sorbitan monolaurate, and nonionic block copolymers of ethylene oxide and propylene oxide such as those marketed by BASF Wyandotte under the name PLURONICS®. When present, such stabilizers comprise from about 0.05% to about 1%, preferably from about 0.1% to about 0.8%, by weight of the composition.

The propellant gas included in the aerosol forms of the compositions of the present invention can be any liquefiable gas conventionally used for aerosol containers. Examples of materials that are suitable for use as propellants are trichlorofluoromethane, dichlorodifluoromethane, dichlorotetrafluoroethane, monochlorodifluoromethane, trichlorotrifluoroethane, dimethyl ether, propane, n-butane and isobutane, used singly or admixed. Water-soluble gases such as dimethyl ether, carbon dioxide, and/or nitrous oxide also can be used to obtain aerosols having reduced flammability.

Water-immiscible, liquified, hydrocarbon and halogenated hydrocarbon gases such as propane, butane and chlorofluorocarbons can be used advantageously to deliver the contents of the aerosol container without the dramatic pressure drops associated with other immiscible gases. Here there is no concern for the head space to be left inside the aerosol container, because the liquified gas will sit on top of the aqueous formulation and the pressure inside the container is always the vapor pressure of saturated hydrocarbon vapor.

Other insoluble, compressed gases such as nitrogen, helium and fully-flourinated oxetanes and oxepanes also are useful to deliver the compositions from aerosol containers. Other means of delivery of the above-described aqueous styling aid compositions include, pump sprayers, all forms of bag-in-can devices, in situ carbon dioxide ($CO_2$) generator systems, compressors, and the like.

The amount of the propellant gas is governed by normal factors well known in the aerosol art. For mousses, the level of propellant is generally from about 3% to about 30%, preferably from about 5% to about 15% of the total composition. If a propellant such as dimethyl ether utilizes a vapor pressure suppressant (e.g., trichlorethane or dichloromethane), for weight percentage calculations, the amount of suppressant is included as part of the propellant.

Other common cosmetic additives can be incorporated with the essential ingredients of the present invention, as long as the basic properties of the hair setting composition are not adversely affected. These additives include, but are not limited to, commonly used fragrances, dyes, opacifiers, pearlescing agents, foam stabilizers, preservatives, water softening agents, acids, bases, sequestering agents, buffers and the like; and will usually be present in weight percentages of less than about 1% each, and about 2% to about 5% in total. The composition vehicle, or carrier, is predominantly water but organic solvents also can be added to the composition in order to solubilize compounds that are not sufficiently soluble in water. Suitable solvents include those that do not react with the ionizable metal salt or the amino-containing compound such as the lower alcohols like ethanol and isopropanol; polyols like glycerol; glycols or glycol ethers, like 2-butoxyethanol, ethylene glycol, ethylene glycol monoethyl ether, propylene glycol and diethylene glycol monomethyl ether; and mixtures thereof. These solvents can be present in the hair setting composition of the present invention in an amount from about 1% to about 75% by weight and, in particular, from about 5% to about 50% by weight, relative to the total weight of the composition.

The compositions can be thickened, for example, with sodium alginate, gum arabic, cellulose derivatives such as methylcellulose, hydroxyethylcellulose, hydroxypropylmethylcellulose and carboxylmethyl-cellulose, and various polymeric thickeners, such as acrylic acid derivaties. It is also possible to use inorganic thickeners such as bentonite. These thickeners are preferably present in the amount from about 0.1% to about 10% by weight and, in particular, from about 0.5% to about 3% by weight, relative to the total weight of the composition.

The compositions also can include anionic, amphoteric or nonionic surfactants, to impart cleansing and/or emulsifying properties to the composition. Likewise, the compositions can contain other emulsifiers, fatty alcohols, humectants and similar materials to provide conditioning properties, aesthetic properties and desirable physical properties to the composition.

For example, representative nonionic surfactants include esters or polyols and sugars; the polyethoxylated and/or polypropoxylated alkylphenols; the polyhydroxylated polyethers of fatty alcohols; and the condensation products of ethylene oxide with long chain mercaptans or long chain amides. Similarly, representative anionic surfactants include alkali metal salts, ammonium salts or salts of amines or amino alcohols of fatty acids such as oleic acid; of the sulfates of fatty alcohols, principally $C_{12}$–$C_{14}$ and $C_{16}$ fatty alcohols; of the sulfates of polyethoxylated fatty alcohols; the alkylbenzenesulfonates, such as those wherein the alkyl moiety has about 12 to about 22 carbon atoms; or the alkylarylpolyether sulfates and monoglyceride sulfates. All these nonionic and anionic surfactants, as well as numerous others not cited here, are well known in the art and are fully described in the literature.

The optional alcohol employed in the composition is an aliphatic straight or branched chain monohydric alcohol having 2 to about 4 carbon atoms. Isopropanol and especially ethanol are preferred. The concentration of the alcohol in the composition should be less than about 20% by weight, and surprisingly can be as low as 0%, preferably 0% to about 10% by weight and more preferably about 5% to about 10% by weight. Some alcohol, in an amount of about 2% to about 10% by weight provides faster drying of the styling aid after application to the hair.

What is claimed is:

1. A method of thermally setting hair consisting essentially of the sequential steps of:
    (a) applying a thermoplastic polyester fixative resin composition, having a pH less than about 5, to the hair prior to configuring the hair in a desired configuration, said polyester having a glass transition temperature of about 20° C. to less than about 120° C. and having the general structure:

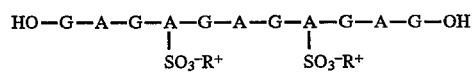

A=an aromatic dicarboxylic acid moiety
G=an aliphatic or cycloaliphatic glycol resin
OH=hydroxy end groups R=H or a monovalent metal; a primary, secondary or tertiary amine; ammonium or an alkanolamine;

(b) contacting the hair with a thermal appliance to heat the applied polyester to its glass transition temperature;

(c) configuring the hair while the polyester is at a temperature of at least its glass transition temperature; and (d) cooling the polyester to a temperature below its glass transition temperature while the hair is in the desired configuration to harden the polyester in the shape of the configured hair.

2. The method of claim 1, wherein the polyester is heated in step (b) to a temperature in the range of about 80° C. to about 120° C.

3. The method of claim 1, wherein the polyester is heated in step (b) with a curling iron and wherein the polyester is cooled by removing the curling iron from hair contact.

4. The method of claim 1, wherein the polyester composition includes a propellant gas and the polyester is applied to the hair in step (a) from an aerosol spray.

5. The method of claim 1, wherein the polyester composition is applied to the hair in step (a) while the hair is wet.

6. The method of claim 5, further including the step of drying the hair in step (b) with heated air while simultaneously heating the polyester to its glass transition temperature.

7. The method of claim 1 further including the step of drying the hair instead (b) prior to configuring the hair while the polyester is at a temperature of at least its glass transition temperature.

8. The method of claim 1, wherein the composition comprises about 30% to about 99.9% by weight water and about 0.1% to about 20% by weight of the thermoplastic polyester fixative resin.

9. The method of claim 8, wherein the composition further includes an ionizable metal salt having a valence of at least II, in an amount sufficient to cross-linked the sulfonate moieties of a plurality of polyester molecules of said thermoplastic polyester.

10. The method of claim 8, wherein the thermoplastic polyester is present in the composition in an amount of about 0.1% to about 5% by weight of the composition.

11. The method of claim 10, wherein the thermoplastic polyester is present in the composition in an amount of about 0.1% by weight to about 2.0% by weight of the composition.

12. The method of claim 1, wherein the polyester includes 5 to 8 $SO_3R$ substituents per polymer molecule.

13. The method of claim 12, wherein the polyester has a weight average molecular weight less than about 200,000.

14. The method of claim 12, wherein the $SO_3R$ substituents are selected from the group consisting of $SO_3H$ and $SO_3M$, wherein M is a monovalent metal.

15. The method of claim 1, wherein G is selected from the group consisting of polyethylene glycol, polypropylene glycol, cyclohexane diol, and cyclopentane diol.

16. The method of claim 1, wherein the polyester has a glass transition temperature in the range of about 20° C. to about 80° C.

17. The method of claim 1, wherein the composition further includes about 1% to about 10% by weight of a hair conditioning agent.

18. The method of claim 1, wherein the composition further includes a surfactant in an amount less than about 5% by weight of the composition.

19. The method of claim 18, wherein the surfactant is present in the composition in an amount less than about 3% by weight of the composition.

20. The method of claim 1, wherein the composition is a mousse composition comprising water, and said polyester in an amount of about 0.1% to about 6% by weight.

21. The method of claim 20, wherein the composition further includes about 5% to about 15% by weight of a propellant gas.

22. The method of claim 9 wherein the metal having a valence of at least two is selected from the group consisting of magnesium, calcium, barium, aluminum, titanium, vanadium, manganese, mercury, cadmium, lead, iron, cobalt, nickel, silver, copper, cerium, hafnium, germanium, zinc, zirconium, and mixtures thereof.

23. The method of claim 9 wherein the ionizable metal salt has an anion selected from the group consisting of a halide, sulfate, nitrate, phosphate, acetate, lactate, and mixtures thereof.

24. The method of claim 9 wherein the ionizable metal salt is selected from the group consisting of aluminum chloride, aluminum sulfate, aluminum lactate, calcium sulfate, cupric chloride, magnesium chloride, zinc chloride, ferric chloride, and mixtures thereof.

25. The method of claim 9 wherein the composition includes an ionizable metal salt in an amount of at least 1.5% of metal based on the weight of the thermoplastic polyester.

26. A method of thermally setting hair consisting essentially of the sequential step of:

(a) applying a thermoplastic polyester fixative resin composition, having a pH less than about 5, to the hair prior to configuring the hair in a desired configuration, said polyester having a glass transition temperature of about 20° C. less than about 120° C. and having the general structure:

$$HO-G-A-G-A-G-A-G-A-G-OH$$
$$\phantom{HO-G-A-G-}| \phantom{A-G-A-G-}|$$
$$\phantom{HO-G-A-G-}SO_3^-R^+ \phantom{A-G-}SO_3^-R^+$$

A=an aromatic dicarboxylic acid moiety
G=an aliphatic or cycloaliphatic glycol resin
OH=hydroxy end groups
R=H or a monovalent metal; a primary, secondary or tertiary amine; ammonium or an alkanolamine;

(b) contacting the hair with a thermal appliance to heat the applied polyester to its glass transition temperature; while configuring the hair while the polyester is at a temperature of at least its glass transition temperature; and (c) cooling the polyester to a temperature below its glass transition temperature while the hair is in the desired configuration to harden the polyester in the shape of the configured hair.

* * * * *